United States Patent [19]

Marston et al.

[11] Patent Number: 5,155,261
[45] Date of Patent: Oct. 13, 1992

[54] PROCESS FOR ACETIC ACID PREPARATION AND HETEROGENOUS CATALYST FOR SAME

[75] Inventors: Charles R. Marston, Indianapolis; Gerald L. Goe, Greenwood, both of Ind.

[73] Assignee: Reilly Industries, Inc., Indianapolis, Ind.

[21] Appl. No.: 787,767

[22] Filed: Nov. 6, 1991

Related U.S. Application Data

[63] Continuation of Ser. No. 616,699, Nov. 20, 1990, abandoned, which is a continuation of Ser. No. 501,356, Mar. 28, 1990, abandoned, which is a continuation of Ser. No. 384,072, Jul. 21, 1989, abandoned, which is a continuation of Ser. No. 265,321, Oct. 27, 1988, abandoned, which is a continuation of Ser. No. 11,286, Feb. 5, 1987, abandoned.

[51] Int. Cl.⁵ .......................................... C07C 45/50
[52] U.S. Cl. .................................................. 562/519
[58] Field of Search ........................................ 562/519

[56] References Cited

U.S. PATENT DOCUMENTS 3,769,329  10/1973  Paulik et al. ............. 560/232
4,328,125  5/1982  Drago et al. ............. 562/519 X

FOREIGN PATENT DOCUMENTS 1538782  1/1979  United Kingdom ............. 560/232

Primary Examiner—Arthur C. Prescott
Attorney, Agent, or Firm—Woodard, Emhardt, Naughton, Moriarty & McNett

[57] ABSTRACT

An improved Monsanto-type process for acetic acid preparation and a heterogeneous-supported catalyst for accomplishing the same, comprising reacting methanol with carbon monoxide under pressure of about 65-80 Bar and temperature of about 170°-200° C. in the presence of methyl iodide and a catalyst comprising an insoluble polymer having pendant free base, N-oxide or quaternized pyridine groups supporting a rhodium species loaded to less than about 10 weight percent (expressed as metal) of the polymer component.

20 Claims, No Drawings

PROCESS FOR ACETIC ACID PREPARATION AND HETEROGENOUS CATALYST FOR SAME

This application is a continuation of application of Ser. No. 07/616,699 filed Nov. 20, 1990 now abandoned, which is a continuation of application Ser. No. 501,356 filed Mar. 28, 1990 now abandoned, which is a continuation of application Ser. No. 384,072 filed Jul. 21, 1989 now abandoned, which is a continuation of application Ser. No. 265,321, filed Oct. 27, 1988 now abandoned, which is a continuation of application Ser. No. 11,286, filed Feb. 5, 1987 now abandoned.

BACKGROUND OF THE INVENTION

This invention relates generally to the fields of catalytic and pyridine chemistry, and in particular, to an improved heterogeneous-supported catalyst and process for the carbonylation of methanol in the production of acetic acid.

From a historical viewpoint, carbonylation and related processes for the preparation of carboxylic acids and esters from corresponding alcohols or their derivatives are long and well known in the art. This is particularly true of the carbonylation of methanol in the production of acetic acid, which has enjoyed a significant worldwide market for many years.

As general background, reference can be made to Kirk-Othmer, *Encyclopedia of Chemical Technology* 1, 135 et seq. (1978), which highlights this history as well as the major contribution by the Monsanto Company in the early 1970's in developing a process for methanol carbonylation based on an iodide-promoted catalyst incorporating rhodium metal complexed with phosphines. This catalyst was homogeneous, and therefore soluble in the reaction medium requiring its recovery from the still bottoms following carbonylation so that recycling of the expensive rhodium metal could be effected. This Monsanto process, as it is known and commonly referred to in the industry, has received widespread acceptance to the extent that the great majority of the world's production of acetic acid is now accomplished by its basic teaching. Considerable publications have appeared over the years describing and analyzing this Monsanto process, including its facets and benefits. The leading U.S. patent for the process appears to be U.S. Pat. No. 3,769,329 issued to Paulik et al. in 1973, which is hereby incorporated and hereby referenced to the extent that any further explanation or understanding of this Monsanto process is required for the purposes of the present application.

There has been limited attention given to this Monsanto process for acetic acid synthesis with regard to possible supported versions of its homogeneous catalyst. Several laboratories have attempted ionic attachments to both organic and inorganic polymers, but with limited success. Although supported catalysts having reactivities approaching their homogeneous analogs have been reported, deactivation of the rhodium by the polymeric support or other difficulties have been the norm rather than the exception. This is somewhat expected from the common experience and thinking in the industry that some deactivation will result when a heterogenous support is employed.

As examples of this work, some of the earliest attempts were to place a rhodium compound on carbon or alumina for use in a vapor phase reaction. In this regard, Jarrell and Gates, *J. Catal.*, 40, 255 (1975) used a standard kind of phosphine-containing polymer to support rhodium for both liquid and gas phase reactions. They reported that the catalyst lost activity rapidly due to rhodium leaching from the support even at exceptionally low temperatures in the range of 85°-95° C. Further attempts are reviewed, for example, in Forster, *Adv. Organomet. Chem.*, 17, 255-267 (1979) and in Scurrell, *Platinum Metals Review*, 21(3), 92-96 (1977).

More recently, another article has described the possibility of supporting a rhodium compound on an ionic resin such as Dowex 1-X8, Bio-Rex 9, or a possible copolymer of styrene and 4-vinylpyridine alkylated with methyl iodide. Drago et al., *Inorg. Chem.*, 20, 641-644 (1981). This article included no experimental results using the suggested polyvinylpyridine derivative catalyst. From the examples that were given, the authors concluded that their ionically-supported rhodium catalyst was approximately equal in catalytic activity to the homogeneous complex, and that leaching of the catalyst could be minimized by suitable choice of solvent and by selecting high resin:rhodium ratios. In all tests reported, however, only low temperatures of 120° C. and low pressures of 80 psi were used. Moreover, it was believed that doubling the amount of supported catalyst (and thus the rhodium present) resulted in a corresponding doubling of the reaction rate, and that an effective method for carrying out the reaction may be to maintain large concentrations of catalyst particularly in a liquid-flow system design.

In a later-issued patent, U.S. Pat. No. 4,328,125, Drago et al. similarly used only mild temperatures at about 120°-130° C. and pressures ranging from less than 60 psi to 160 psi in one example. These conditions, and particularly the low temperatures, are wholly impractical for any commercial use in acetic acid production, and are specifically far outside the Monsanto process conditions of temperatures at about 170°-200° C. and pressures at about 65-80 Bar. As a result, the reaction rates are so low as compared to the homogeneous process that large reactions with increased material costs, long residence times, and resulting low space-time yields would be needed to have any hope of producing a commercial product. These mild Drago et al. conditions are nonetheless required by most ion exchange resins which are not stable, for example, at elevated temperatures above 170° C. and approaching 200° C. The patent concludes that large concentrations of catalysts relative to liquid, particularly in a flow process, will result in very rapid reaction rates with the process preferably being carried out at these lower temperatures under less corrosive conditions than processes using conventional homogeneous catalysts. Although polyvinylpyridines, as such, are mentioned at one point in the Drago et al. patent, no examples are given of their preparation or use. The examples are instead limited to one example of a polystyrene bound pyridine and to commercially available anionic exchange resins identified as Amberlite IRA-400 and Dowex 1-X8 which are used in applications as catalysts for the hydroformulation of olefins.

Importantly, there is no disclosure or suggestion in this Drago et al. article and Patent, or in any other reference known, evidencing an appreciation of any significance of the degree or amount of metal loading of the catalyst as it relates directly to reaction performance, nor is there any teaching, disclosure, or suggestion in any reference known to Applicants evidencing an appreciation of any significance of a particular type, class or characteristic of polymer support as it relates directly to reaction performance. The only beliefs of this type known to have been reported, as already mentioned for Drago et al., are in some direct dependence of reaction rate on increasing catalyst concentrations or amount and in some possible effect on leaching by increasing the resin:rhodium ratio.

SUMMARY OF THE INVENTION

Contrary to this prior teaching, Applicants have discovered an unexpected activation of the rate of carbonylation of methanol to acetic acid in a commercial process, but using a heterogeneous-supported catalyst and lowering the metal loading to levels significantly below those previously used or thought suitable in a homogeneous or supported commercial setting. Applicants have also discovered a heterogeneous catalyst which accomplishes this result, comprising an insoluble polymer having pendant free base, N-oxide or quaternized pyridine groups or a combination thereof supporting a rhodium species loaded to less than about 10 weight percent (expressed as metal) of the polymer component. Most preferred to date has been a porous cross-linked 4 or 2- vinylpyridine copolymer in the free base or N-oxide form which has been quaternized either preformed or in situ with an alkyl halide such as methyl iodide and loaded at about 2 weight percent by reaction with a rhodium salt such as rhodium chloride trihydrate in an initial or generation run. Both methyl iodide and rhodium chloride trihydrate are commonly used components in the homogeneous Monsanto process.

Another aspect of this invention is the effective use of Applicants' heterogenous catalyst in a commercial improved Monsanto process for preparing acetic acid by reacting methanol with carbon monoxide in the presence of a methyl iodide promoter and an otherwise homogeneous rhodium source supported on the insoluble polymer catalyst described and claimed herein. This process proceeds under pressures of about 65–80 Bar and temperatures of about 170°–200° C. which have definite and proven commercial practicability, unlike the mild conditions of prior art references such as Drago et al. Even so, Applicants' insoluble polymers exhibit excellent stability at such elevated conditions and is further beneficial in their selectivity, in their ability to be formed and regenerated in situ, and in their ease of recovery and repeated recyclability without significant losses of reactivity due to rhodium leaching or otherwise. Moreover, as stated above, these catalysts exhibit an unexpected activation of the rate of methanol carbonylation which is highly beneficial and has resulted in productions of acetic acid exceeding four-fold improvements over those achieved either with homogeneous catalysts or with any heterogeneous catalysts previously reported.

DESCRIPTION OF THE PREFERRED EMBODIMENTS

For the purposes of promoting an understanding of the principles of the invention, reference will now be made to several embodiments illustrated in the examples and specific language will be used to describe the same. It will nevertheless be understood that no limitation of the scope of the invention is thereby intended, such alterations and further modifications in these embodiments, and such further applications of the principles of the invention as described herein being contemplated as would normally occur to one skilled in the art to which the invention relates.

As already described, one aspect of Applicants' invention is an improved heterogeneous polymer catalyst for use in such reactions as the carbonylation of methanol to form acetic acid. This catalyst comprises an insoluble polymer having pendant free base, N-oxide or quaternized pyridine groups or a combination thereof and supporting a rhodium species loaded to less than about 10 weight percent (expressed as metal) of the polymer component. Most preferred has been a porous cross-linked 4- or 2-vinylpyridine copolymer in the free base or N-oxide form which has been quaternized either preformed or in situ with an alkyl halide such as methyl iodide and loaded at about 2 weight percent by reaction with a rhodium salt such as rhodium chloride trihydrate in an initial or generation run.

More specifically, of the testing performed to date the polymers of choice have been porous cross-linked poly(4- and 2- vinylpyridine) copolymers such as those commercially available under the Reillex TM family of trademarks from Reilly Tar & Chemical Corporation of Indianapolis, Ind. In these Reillex TM copolymers, substantial pyridine rings are attached directly at their 4- or 2- positions to the polymer's backbone which is in turn cross-linked with some percentage of divinylbenzene being present. Reillex TM 425, for example, is the most preferred polymer support tested to date, being a 25% cross-linked copolymer of 4-vinylpyridine and a commercially available divinylbenzene and exhibiting a convenient insoluble bead form, high porosity, good thermal stability, and high concentration of metal binding sites. Although bead size and other physical characteristics of these polymer supports have not been shown to be critical, it is noted that Reillex TM 425 is typically available in bead sizes of approximately 18–50 mesh. It is also noteworthy that the temperature stability for extended use of the Reillex TM 425 polymer is about 260° C., which comfortably exceeds the requirements for most, if not all, reactions usefully catalyzed by metal complexes of this type. It is particularly practicable in the commercial carbonylation of methanol to make acetic acid which Applicants prefer to run at the common Monsanto pressures of about 65–80 Bar and temperatures of about 170°–200° C. This is in direct contrast to most ion exchange resins, such as many of those used in the cited references above, which are not stable at such elevated temperatures.

Other preferred polymers include, for example, other cross-linked poly(4- and 2-vinylpyridine) copolymers such as those commercially available under the Reillex TM 402 and 225 trademarks also from Reilly Tar & Chemical Corporation. Of these, Reillex TM 225 is a 25% cross-linked copolymer of 2-vinylpyridine and a commercially available divinylbenzene. In other relevant respects, Reillex TM 225 is similar in its performance to the Reillex TM 425 described above. Reillex TM 402 is a 2% cross-linked copolymer of 4-vinylpyridine and a commercially available divinylbenzene. Reillex TM 402 is a granular powder, in contrast to the bead forms of Reillex TM 225 and 425, with a particle size of about 60 mesh and a slightly lower, but still acceptable, maximum temperature for extended use of about 225° C.

For more detail as to the chemical make-up and characteristics of these or other Reillex TM polymers, reference can be made to relevant literature available either through the industry or from the manufacturer itself.

One such reference is a brochure published by the Reilly Tar & Chemical Corporation entitled *Reillex ™: A New Family of Cross-linked Polyvinylpyridines from Reilly* (*Reillex ™ Report* 2, 1986), which is hereby incorporated by reference in all respects relevant and material to the application at hand.

In addition to these several Reillex ™ polymers, other polymers which contain pyridine, or pyridyl, groups to support the rhodium metal and which exhibit these same or similar desirable properties are also suitable for use in the Applicants' preferred catalysts as described herein. These include polymers that may be or have been commercially marketed, such as the KEX ™ -316 polymeric amine resin of Example 13, as well as others that can be readily prepared by known procedures such as those described in Examples 5, 6 and 7 below. Derivative forms of these free base polymers are also suitable in Applicants' catalysts, an example being the N-oxide form which has tested very effectively and possibly even preferred, as appears in several examples below.

In this regard, only certain limitations as discussed herein are understood to apply to such suitable polymers. One is that they be insoluble in the reaction mixture, whether this insolubility results from molecular weight, cross-linking by chemical or radiation means, or some other technique or procedure. Another is that they exhibit stability at the elevated temperatures indicated herein in order to function effectively and at a commercial level in Applicants' improved Monsanto-type process. Still another is that they contain an effective amount of pendant pyridine, or pyridyl as it may be referred to, groups sufficient in their quaternized form to support and complex with the rhodium metal at the specified loading levels in order to provide the beneficial catalytic activity achieved to a great extent by Applicants' preferred catalysts described herein. Additional pyridine functionality may provide further benefits such as a greater number of bonding sites or increased selectivity in a particular reaction under consideration, but is not seen as necessary from the testing performed to date.

As to what constitutes such an effective or sufficient amount of pendant pyridine, or pyridyl, groups, this will vary of course depending upon many factors including the particular polymer and reaction involved. The equipment used is also a factor as lesser amounts of pyridine functionality may be acceptable where larger quantities of catalyst are used or where contact times, flow rates or other reaction conditions are adjusted to account for the lower levels of complexed rhodium on the polymer support. Experiments to date have suggested that polymers with pyridyl contents as low as 10% by weight are still effective to provide acceptable catalytic activity, as shown in Example 14 below. More preferred are pyridine levels of at least about 20-25% because of the additional reactive sites they provide, and most preferred have been pyridine amounts in excess of about 50% as exhibited in the Applicants' most preferred Reillex ™ polymers.

Once the desired polymer is selected, Applicants' preferred catalyst is prepared by reacting this polymer support with an alkyl halide and a rhodium compound, both of which are readily accomplished by standard procedures and using known components for such reactions. For example, preferred to date has been simply adding an amount of the insoluble polymer resin beads to what would otherwise constitute a homogeneous medium for the methanol carbonylation reaction under the Monsanto teaching. This includes placing methanol and carbon monoxide as feed stocks in a pressure vessel along with a rhodium species and with an iodide promoter. In this regard, methyl iodide is preferred as it serves both as a promoter and as the alkyl halide needed to quaternize the Applicants' polymer component. Rhodium chloride trihydrate ($RhCl_3.3H_2O$) is the rhodium compound of choice, although other suitable ones are known and available.

This reaction mixture is then subjected to standard carbonylation conditions, such as those discussed in Paulik et al., U.S. Pat. No. 3,769,329 incorporated hereinabove, for the underlying Monsanto process reaction, in what amounts to a catalyst generation run. In particular, the reactor is pressurized with the carbon monoxide and heated to a temperature such that the heterogeneous catalyst forms in situ and the carbonylation reaction proceeds. It has also been preferred to use a solvent such as acetic acid. Work-up of the reaction is then accomplished by simply decanting the converted acetic acid product, filtering the quaternized polymer-supported rhodium catalyst from the remaining unconverted medium, and then washing the catalyst beads with methanol and recovery of the catalyst for subsequent recycling.

As with the components described above, preferred reaction conditions used for the Applicants' catalyst generation run as well as for subsequent carbonylations are only significant in that they parallel the conditions commonly known and used in homogeneous Monsanto process reactions. In this regard, as used throughout this specification and claims, the phrase "Monsanto process" is meant to define this well-understood carbonylation reaction to produce acetic acid including the various reaction components and conditions which have been long known to those of ordinary skill in this art. With this background, as highlighted by the specific disclosures herein, it is to be understood that one aspect of the Applicants' invention is an improvement to this well-known Monsanto process incorporating a heterogeneous polymer catalyst complex which has achieved unexpected and enhanced results as to reaction performance over either the homogeneous Monsanto process or any other attempts to vary it as found any known literature or other references. Specifically in the case of the preferred conditions for the reaction, preferred pressures have been the same Monsanto pressures of about 65-80 Bar and temperatures of about 170°-200° C. Most preferred has, in turn, been a pressure of about 75 Bar and a temperature of about 175° C., although these conditions are difficult to maintain with precision and need to be monitored during the reaction. For example, carbon monoxide needs to be replenished as consumption lowers the internal or head pressure to about 65 Bar. Exothermic temperature overruns may also be encountered in view of the increased activation experienced with Applicants' catalysts, particularly in the early stages of a run. Overall, however, these preferred conditions result in a very commercially practicable reaction which produces high conversion and selectivity of acetic acid using a catalyst that is easily handled and recovered by simple filtration, and is recyclable without significant loss of activity.

As to the reaction components, an important aspect of Applicants' discovery has been the observation previously mentioned that by using the Applicants' preferred polymers as described above and by lowering the level or degree of rhodium loading of the catalyst to less than about 10 weight percent, an unexpected activation results. Evidence of rhodium leaching even upon successive recycles of the same catalyst is minimal. At the same time, experimental runs have shown up to and exceeding four-fold increases in reaction rates using Applicants' insoluble polymer catalysts over results obtained in homogeneous or other reported heterogeneous runs. For example, the space-time yield of acetic acid formation using the homogeneous Monsanto process has been reported to be from about 1.5–2.0 mol/L,hr of catalyst solution. Calculations from data given in example 1 of the Monsanto (Paulik et al.) patent agree with this range, giving a reaction rate yield of 1.6 mol/L, hr. Without further modification, Applicants' have encountered experimental runs with their Reillex TM -supported catalysts varying from about 7.0–8.0 mol/L, hr, thereby accounting for over a four-fold increase in performance. This unexpected activation or promotion of the reaction using the Applicants' low-loaded polymer support is not taught, disclosed or suggested by any known prior references or reports.

Moreover, recycling and regeneration of Applicants' preferred catalysts are readily accomplished using known methods and procedures. For example, when an acceptable conversion level has occurred in a given batch run, whether this is determined by elapsed time or by monitoring carbon monoxide consumption or some other parameter, the vessel need only be cooled and vented of residual pressure after which the acetic acid product is recovered by simple decanting. The supported catalyst is then either filtered and possibly washed with fresh methanol for later reuse or the reactor is simply recharged with feedstock as needed, repressurized and a second reaction begun.

As catalyst lifetimes are better understood through working with a particular catalyst in repeated recycling in either a laboratory or a commercial setting, it may be further desirable to regenerate the catalyst from time to time through the addition possibly of an amount of methyl iodide or another component in the feedstock. Continuous reaction processes are also practicable for Applicants' preferred catalysts in view of their insolubility and resistance to leaching or other degradation. Such processes can be designed and implemented using common and known procedures in the art.

For the purposes of further promoting a better understanding of the catalysts and processes of the present invention, reference will now be made in the Examples below to specific instances of their preparation and use. These examples are exemplary only, and no limitation of the scope or breadth of Applicants' invention is intended thereby.

EXAMPLE 1

Catalyst Generation

An insoluble polymer catalyst of Applicants' preferred embodiment was prepared under known Monsanto carbonylation conditions as stated above. For example, 19.6 g of poly(4-vinylpyridine) N-oxide in the form of Reillex TM 425, 0.4 g of $RhCl_3.3H_2O$, 100 g of methanol, 28.8 g of methyl iodide, and 198 g of acetic acid were placed in a 600 cc Teflon ® lined stainless steel autoclave to which carbon monoxide (CO) was admitted on demand at pressures of 65–80 Bars. The mixture was heated at 170°–200° C. for two hours after which the reactor was cooled and vented. The solid polymeric quaternized catalyst was isolated by decantation of the liquid followed by trituration of the solid beads with fresh methanol, and was identified by metal uptake and material balance as containing a weight of rhodium metal equal to eight tenths of one percent (0.8%) of the weight of polymer present.

Methanol Carbonylation 20 g of poly(4-vinylpyridine) N-oxide-supported rhodium catalyst prepared above, 100 g of methanol, 28.8 g of methyl iodide, and 198 g of acetic acid were then placed in the 600 cc Teflon TM lined stainless steel autoclave. The temperature was raised to 180° C. while CO was admitted upon demand at a level of between 65–80 Bars. The time required for 50% of the methanol to be converted to acetic acid was 20 minutes. The selectivity to acetic acid was determined to be greater than 99%. The average rate of carbonylation checked over the range of 0–35% conversion, which is a common standard to work from in this area, was determined to be 40.8 (mol AcOH/mol Rh, min) which is extremely high for a commercial production, and better than a six-fold increase over reported and calculated values for the homogeneous Monsanto process as shown on Table 1. The rate of the reaction expressed as mol AcOH/L, hr was also determined at the stages of 30% and 50% conversion. These values were 10.9 and 9.8 mol AcOH/L, hr, respectively, which confirmed the continued reactivity of the applicant's catalyst over time as greater conversions are achieved. This is contrasted dramatically by the low reaction rate of 1.3 mol AcOH/L hr calculated for a homogeneous reaction to proceed to 30% conversion, and even more by its decrease by a factor of 10 to only 0.1 mol AcOH/L, hr to obtain a 50% conversion using the homogeneous catalyst mixture. This decrease in reaction rate over time for the homogeneous reaction is also evident from analysis of the rate and time data in Table 1.

EXAMPLE 2-13

The reaction conditions and feedstocks, both for catalyst generation and use of Example 1, were substantially repeated employing different insoluble polymer supports for the catalysts as more particularly described in Table 1. Specifically, the reactions detailed in Examples 2–7 and 13 were run at 180°–185° C. and at a CO pressure of 65–85 Bars, using feedstocks of 100 g methanol (MeOH), 19.6 g of the indicated insoluble polymer support, 28.8 g of methyl iodide as a promoter and quaternizing agent, 0.4 g of rhodium chloride trihydrate ($RhCl_3.3H_2O$), and 198 g of acetic acid functioning as a solvent for the reactions. The degree or level of rhodium loading in Examples 2–7 and 13 was about 0.8% of the weight of polymer used, and methanol conversions in these examples exceeded 99% and in each case selectivity to acetic acid was greater than 98%. In each Example, the run reported is the first recycle following the initial catalyst generation run. Example 8 was added to provide a reference based on a homogeneous Monsanto run with the results indicated being taken from the Kirk-Othmer reference cited above and verified by calculation from Example 1 of the Paulik et al. patent.

As to Examples 5, 6 and 7, the specific polyvinylpryidine supports were prepared according to the same general procedure as outlined in the first part of Example 14 below. The only modifications were that the appropriate vinylpyridine monomer was substituted and that the ratio of crosslinking agent to each vinylpyridine was varied to achieve the particular degree of loading expressed in the preceding paragraph for each of the Examples. Essentially, this involves substituting additional amounts of the several vinylpyridines for the styrene used in Example 14, in order to achieve the substantially decreased level of loading.

In Examples 9 and 10, only 1.7 g of the designated polymer support was employed, which resulted in a catalyst having a weight of rhodium metal equal to 9.2% of the polymer employed. Although a rate lower than the homogeneous reaction was noted between 0-35% conversion, this rate did not decrease significantly over time due to rhodium leaching or other causes, thereby resulting in a significantly shorter time being required to arrive at 50% conversion to acetic acid. This result is commercially significant as it will permit longer batch reactions and with higher percentage productions of desired product and less-frequent regenerations of the batch medium due to deactivation of catalyst as seen in the homogeneous reaction.

In Examples 11-12, 7.6 g and 3.1 g of the designated polymer supports were employed, which produced catalysts having rhodium metal loading levels equal to about 2.1% and 5% of the polymer used, respectively. As with the above examples, differing degrees of activation or promotion of the underlying reaction were achieved in these further embodiments of the Applicants' invention having commercial significance as described above from the homogeneous or any other reported heterogeneous run. Applicants saw no leaching of rhodium metal in their experiments. In Example 13, the polymer used was KEX TM -316 which is a lightly cross-linked polyvinyl pyridine commercially available pyridine commercially available from Koei Chemical Company Ltd. of Osaka, Japan. As experienced with the more-preferred Reillex TM polymers, the catalyst of Example 13 also evidenced significant improvements over the homogeneous run of Example 8.

As with Example 1 above, rates of reaction were calculated for Examples 3 and 9 expressed as mol AcOH/L,hr for both 30% and 50% conversion for the purpose of comparing them to the homogeneous reaction. These calculations were made from the first recycled runs using a 2% RhCl.3H2O loading in Examples 1, 3 and 8 and a 20% loaded polymer in the case of Example 9. With Example 3, the respective 30% and 50% conversion rates were 5.4 and 5.5 mol AcOH/L,hr. These again showed sizable improvements over the homogeneous rates of 1.3 and 0.1, as well as evidencing no drop in reactivity over time. In Example 9, the calculated rates were 0.7 and 0.4 mol AcOH/L,hr, which although not quantitatively better than the homogeneous reaction up to a 30% conversion, does show a marked improvement in carrying the reaction to 50% conversion. No deactivation of the catalyst therefore occurred, as was experienced in homogeneous and many prior-reported heterogeneous attempts.

TABLE 1

| Example | Polyvinylpyridine Support | Reaction Rate 0-35% conversion (mol AcOH/mol Rh, min) | Reaction Time 50% conversion |
|---|---|---|---|
| 1 | Reillex TM 425 N-oxide | 40.8 | 20 min |
|   | Reillex TM 425 N-oxide (2nd recycle) | 41.2 | 20 min |
| 2 | Reillex TM 402 N-oxide | 24.8 | 30 min |

TABLE 1-continued

| Example | Polyvinylpyridine Support | Reaction Rate 0-35% conversion (mol AcOH/mol Rh, min) | Reaction Time 50% conversion |
|---|---|---|---|
| 3 | Reillex TM 425 | 22.6 | 45 min |
|   | Reillex TM 425 (2nd recycle) | 22.8 | 45 min |
|   | Reillex TM 425 (3rd recycle) | 23.6 | 45 min |
| 4 | Reillex TM 402 | 19.0 | 55 min |
| 5 | Cross-linked poly-2-vinylpyridine | 14.2 | 50 min |
| 6 | Cross-linked poly-6-methyl-2-vinylpyridine | 7.4 | 60 min |
|   | Cross-linked poly-6-methyl-2-vinylpyridine (2nd recycle) | 11.6 | 45 min |
| 7 | Cross-linked poly-2-vinylpyridine N-oxide | 7.3 | 1 hr 45 min |
| 8 | none (homogeneous) | 6.3 | 5 hrs 30 min |
| 9 (b) | Reillex TM 425 | 4.4 | 4 hrs 50 min |
|   | Reillex TM 425 (2nd recycle) | 3.3 |   |
|   | Reillex TM 425 (3rd recycle) | 2.6 |   |
|   | Reillex TM 425 (4th recycle) | 2.0 |   |
| 10 (b) | Reillex TM 425 N-oxide | 4.5 | N/A |
| 11 (c) | Reillex TM 425 | 24.3 | 30 min |
| 12 (d) | Reillex TM 425 | 12.5 | 1 hr 12 min |
| 13 | KEX TM -316 | 25.7 | 30 min |

(a) Unless otherwise specified all reactions are run at 180-185° C. at a CO pressure of 65-85 Bars with 100 g MeOH, 19.6 g of polymer, 28.8 g of methyl iodide as promoter, 0.40 g RhCl3 3H2O in the catalyst (0.8% loadings as metal) and 198 g of acetic acid as solvent. All conversions were greater than 99% and all selectivities greater than 98% unless noted. Initial runs reported are the first recycles after the generation runs.
(b) 1.7 g Polymeric Support (9.2% loading as metal)
(c) 7.6 g Polymeric Support (2.1% loading as metal)
(d) 3.1 g Polymeric Support (5.0% loading as metal)

EXAMPLE 14

Preparation of a Crosslinked Polymer Containing 10% 4-Vinylpyridine

A monomer solution containing 10 g of 4-vinylpyridine, 31.3 g of commercial divinylbenzene (80% DVB), 58.7 g of styrene, 60 g of toluene, and 0.5 g of benzoyl peroxide was added to 300 ml of an aqueous solution containing 1% hydrocellulose, 10% sodium chloride and 0.04% sodium hydroxide. The two phase system was stirred at a moderate rate and heated to 70° C. for 8 hours. The heterogeneous mixture was cooled, filtered, and the crosslinked polymer washed with water and then methanol. The moist solid polymer was then dried for 6 hours at 110° C.

Catalyst Generation and Carbonylation of Methanol

Catalyst generation and recycle reactions were carried out in a manner identical with the methods and quantities employed in Examples 1-13 except 35 g of the insoluble polymer component described above was employed as the catalyst support. Carbon monoxide was consumed at a rate comparable to rates observed under the preferred conditions. Production of acetic acid in high conversion was confirmed under the conditions of this Example.

EXAMPLE 15

Adding Reillex TM 425.MeI to Homogeneous Monsanto Reaction

A homogeneously catalyzed Monsanto reaction was initiated as in Example 8 above, and the rate of catalyst turnover was measured at 5.1 mol AcOH/mol Rh, min. at 20% conversion. The reactor was cooled and vented and 10 g of poly(4-vinylpyridine)(Reillex TM 425) already quaternized with methyl iodide was added to the reaction mixture. The autoclave was resealed and charged with CO at 50 Bar, the temperature was raised to 180° C. and the rate of catalyst turnover was measured while admitting CO upon demand at 65-80 Bar. The turnover rate was then determined to be 26.6 mol AcOH/mol Rh, min. at 35% conversion, which amounted to about a five-fold rate increase in the rate of formation of acetic acid over the homogeneous run.

EXAMPLE 16

Catalyst Generation 12 g of Amberlyst TM A-21 polymeric amine resin was added to a mixture of 100 g of MeOH, 28.8 g of MeI, 198 g of acetic acid and 0.4 g of $RhCl_3.3H_2O$. CO was then introduced upon demand at 65-80 Bars and at a temperature of 180° C. was maintained for one hour. The Amberlyst TM resin-supported catalyst showed similar reaction velocities (24.5 mol AcOH/mol Rh, min.) to those observed with the Reillex TM 425 and 402 supported catalysts of the above examples during catalyst generation.

Nonrecyclability of Amberlyst TM Resin

The solid Amberlyst TM A-21 supported catalyst was separated from the above mixture by filtration and added to a solution of 100 g MeOH, 28.8 g of MeI and 198 g of acetic acid to which CO was introduced upon demand at 65-85 Bars at a temperature of 180° C. The observed rate of CO consumption at 0-35% conversion was only 3.5 mol CO/initial mol Rh, min., which evidenced a lessor ability of this catalyst to be recycled after generation.

We claim:

1. A commercial process for preparing acetic acid, comprising the step of reacting methanol with carbon monoxide under pressures of about 65-80 Bar and temperature of about 170°-200° C. in the presence of an iodide promoter and a catalyst comprising an insoluble polymer having pendant free base, N-oxide or quaternized pyridine groups supporting a rhodium species loaded to less than about 10 weight percent (expressed as metal) of the polymer component.

2. The process of claim 1 wherein the polymer of said reacting is a copolymer derived from a vinylpyridine.

3. The process of claim 2 wherein the vinylpyridine polymer of said reacting is 4-vinylpyridine.

4. The process of claim 2 wherein the vinylpyridine polymer of said reacting is 2-vinylpyridine.

5. The process of claim 3 wherein the polymer of said reacting is poly(4-vinylpyridine) cross-linked with 2% divinylbenzene.

6. The process of claim 3 wherein the polymer of said reacting is poly(4-vinylpyridine) cross-linked with 25% divinylbenzene.

7. The process of claim 4 wherein the polymer of said reacting is poly(4-vinylpyridine) cross-linked with 25% divinylbenzene.

8. The process of claim 2 wherein the rhodium species of said reacting is rhodium chloride trihydrate.

9. The process of claim 2 wherein the polymer of said reacting contains at least about 50% by weight of pendant pyridine groups.

10. The process of claim 2 wherein said reacting step additionally comprises the substeps of:
    charging a pressure vessel with the liquid reaction components;
    pressurizing the mixture to about 65-80 Bars with carbon monoxide; and
    heating the mixture to about 170°-200° C.

11. The process of claim 10 additionally comprising replenishing the vessel with carbon monoxide to about 65-80 Bar during said heating.

12. The process of claim 10 additionally comprising recovering the polymer-supported rhodium catalyst after said pressurizing and heating.

13. The process of claim 12 wherein said recovering additionally comprises decanting the acetic acid product from the reaction mixture after the vessel has been cooled and vented; and
    filtering the insoluble polymer-supported rhodium catalyst from the reaction mixture.

14. The process of claim 10 additionally comprising regenerating and recycling the catalyst after said reacting, including the steps of:
    separating at least a portion of the liquid acetic acid product from the reaction vessel mixture after the vessel has been cooled and vented;
    recharging the vessel with additional amounts of the liquid reactants; and
    repeating said pressurizing and said heating steps.

15. The process of claim 14 wherein said separating, recharging and repeating steps are carried out continuously.

16. The process of claim 1 wherein said reacting step is such as to achieve about 100% conversion from methanol at about 99% selectivity to acetic acid.

17. The process of claim 1 wherein said reacting step is such as to achieve an enhanced reaction rate in excess of about 5 mol AcOH/L, hr.

18. The process of claim 1 wherein said reacting step is such as to achieve an enhanced reaction rate of at least four-fold over a homogeneous-catalyzed reaction.

19. The process of claim 1 wherein said reacting step is such as to achieve about 50% conversion of methanol to acetic acid in less than about one hour.

20. The process of claim 1 wherein said reacting step is such as to achieve an average reaction rate from about 0-35% conversion of at least about 10 mol AcOH/mol Rh, min.

* * * * *